(12) United States Patent
Krupnik et al.

(10) Patent No.: US 9,295,430 B2
(45) Date of Patent: Mar. 29, 2016

(54) OPERATOR CONTROLLED MIXED MODALITY FEEDBACK

(71) Applicant: BIOSENSE WEBSTER (ISRAEL), LTD., Yokneam (IL)

(72) Inventors: Ronen Krupnik, Karmiel (IL); Liron Shmuel Mizrahi, Kiryat Bialik (IL); Roy Urman, Karkur (IL)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 549 days.

(21) Appl. No.: 13/761,207

(22) Filed: Feb. 7, 2013

(65) Prior Publication Data

US 2014/0221768 A1    Aug. 7, 2014

(51) Int. Cl.
*A61B 5/00* (2006.01)
*A61B 18/14* (2006.01)
*A61B 18/00* (2006.01)
*A61B 19/00* (2006.01)

(52) U.S. Cl.
CPC .............. *A61B 5/7455* (2013.01); *A61B 5/6847* (2013.01); *A61B 18/1492* (2013.01); *A61B 2018/00303* (2013.01); *A61B 2018/00357* (2013.01); *A61B 2018/00791* (2013.01); *A61B 2018/00839* (2013.01); *A61B 2019/2292* (2013.01); *A61B 2019/465* (2013.01); *A61B 2019/5251* (2013.01)

(58) Field of Classification Search
CPC ............................ A61B 5/7455; A61B 5/6847
See application file for complete search history.

(56) References Cited

U.S. PATENT DOCUMENTS

| | | | |
|---|---|---|---|
| 5,391,199 | A | 2/1995 | Ben Haim |
| 5,443,489 | A | 8/1995 | Ben-Haim |
| 5,558,091 | A | 9/1996 | Acker et al. |
| 5,944,022 | A | 8/1999 | Nardella et al. |
| 5,983,126 | A | 11/1999 | Wittkampf |
| 6,172,499 | B1 | 1/2001 | Ashe |
| 6,177,792 | B1 | 1/2001 | Govari et al. |
| 6,239,724 | B1 | 5/2001 | Doron |

(Continued)

FOREIGN PATENT DOCUMENTS

| | | |
|---|---|---|
| WO | WO 96/05768 A1 | 2/1996 |
| WO | WO 2005/084542 A1 | 9/2005 |

OTHER PUBLICATIONS

European Search Report dated Mar. 20, 2014 for corresponding application No. EP 14164118.

*Primary Examiner* — Robert N Wieland
(74) *Attorney, Agent, or Firm* — Dergosits & Noah LLP; Todd A. Noah (57) ABSTRACT

Apparatus, including a flexible insertion tube having a distal end for insertion into a body cavity, a first sensor in the distal end configured to acquire a first signal from the cavity during a medical procedure, and a second sensor in the distal end configured to acquire a second signal from the cavity during the procedure. The apparatus also includes a display, and a processor configured to present, on the display, first and second measurements corresponding to the first and second signals, and to accept an input selecting one of the presented measurements so as to generate a selected measurement. The apparatus additionally includes a handle coupled to the tube's proximal end, and a haptic feedback device attached to the handle configured to provide, under direction of the processor, a tactile feedback in response to the selected measurement while deemphasizing a presentation of the selected measurement.

17 Claims, 4 Drawing Sheets

(56) References Cited

U.S. PATENT DOCUMENTS

| | | |
|---|---|---|
| 6,332,089 B1 | 12/2001 | Acker |
| 6,456,864 B1 | 9/2002 | Swanson et al. |
| 6,484,118 B1 | 11/2002 | Govari |
| 6,618,612 B1 | 9/2003 | Acker |
| 6,690,963 B2 | 2/2004 | Ben Haim |
| 6,788,967 B2 | 9/2004 | Ben-Haim et al. |
| 2002/0065455 A1 | 5/2002 | Ben Haim |
| 2003/0120150 A1 | 6/2003 | Govari |
| 2004/0068178 A1 | 4/2004 | Govari |
| 2006/0058854 A1 | 3/2006 | Abrams et al. |
| 2007/0100332 A1 | 5/2007 | Paul |
| 2007/0153331 A1 | 7/2007 | Ueda et al. |
| 2009/0030332 A1 | 1/2009 | Schecter |
| 2009/0093806 A1 | 4/2009 | Govari |
| 2009/0138007 A1 | 5/2009 | Govari |
| 2009/0248042 A1 | 10/2009 | Kirschenman |
| 2010/0073150 A1 | 3/2010 | Olson et al. |
| 2012/0184955 A1 | 7/2012 | Pivotto et al. |
| 2012/0197655 A1 | 8/2012 | Debgupta et al. |
| 2012/0232547 A1 | 9/2012 | Cohen |
| 2013/0274712 A1* | 10/2013 | Schecter ................. 604/510 |
| 2013/0321262 A1* | 12/2013 | Schecter ................. 345/156 |
| 2014/0243660 A1* | 8/2014 | Klinder et al. ............ 600/424 |
| 2015/0067605 A1* | 3/2015 | Zambetti et al. ............ 715/830 |

\* cited by examiner

OPERATOR CONTROLLED MIXED MODALITY FEEDBACK

FIELD OF THE INVENTION

The present invention relates generally to invasive probes, and specifically to a system that conveys operator controlled visual and tactile feedback during a medical procedure.

BACKGROUND OF THE INVENTION

A wide range of medical procedures involves placing objects, such as sensors, tubes, catheters, dispensing devices and implants, within a patient's body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332, 2009/0093806 and 2009/0138007, whose disclosures are incorporated herein by reference, describe methods of sensing contact pressure between the distal tip of a catheter and tissue in a body cavity using a force sensor embedded in the catheter.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention an apparatus, including a flexible insertion tube including a distal end for insertion into a body cavity, a first internal sensor mounted in the distal end and configured to acquire a first signal from the body cavity during a medical procedure, and a second internal sensor mounted in the distal end and configured to acquire a second signal from the body cavity during the medical procedure. The apparatus also includes a display, and a processor configured to present, on the display, first and second measurements corresponding to the first and second signals, and to accept an input selecting one of the presented measurements so as to generate a selected measurement. The apparatus further includes a handle coupled to a proximal end of the flexible insertion tube, and a haptic feedback device fixedly attached to the handle and configured to provide, under direction of the processor, a tactile feedback in response to the selected measurement while a presentation of the selected measurement is deemphasized on the display.

In some embodiments, the first and the second sensors are selected from a list including a position sensor, a force sensor, a temperature sensor and an electrode configured to measure electrical potential. In additional embodiments, the tactile feedback includes a vibration, and the haptic feedback device is configured to vary one of a frequency and an amplitude of the vibration.

In further embodiments, the processor is configured to accept an additional input selecting an additional one of the presented measurements so as to generate an additional selected measurement, and to deemphasize an additional presentation of the additional selected measurement on the display. In some embodiments, an additional haptic feedback device may be affixed to the handle and configured to provide, under direction from the processor, an additional tactile feedback in response to the additional selected measurement.

In supplementary embodiments, the processor is configured to deemphasize the selected measurement by applying an attribute selected from a list including removing the selected measurement from the display, presenting the selected measurement using a predetermined font size, presenting the selected measurement using a predetermined color, and presenting the measurement using a predetermined brightness.

In additional embodiments, the processor is configured to receive, from a device external to the flexible insertion tube, a third signal, and to present on the display a third measurement corresponding to the third signal, and wherein the input selects the third measurement. In some embodiments, the device is selected from a list including a blood pressure module, an irrigation module, an ablation module, an electrocardiography module and a timer module.

There is also provided, in accordance with an embodiment of the present invention, a method, including generating, during a medical procedure, first and second measurements corresponding to first and second signals received from first and second sensors mounted on a distal end of a flexible insertion tube configured for insertion into a body cavity, presenting, on a display, the first and the second measurements, accepting an input selecting one of the presented measurements so as to generate a selected measurement, and providing, by a haptic feedback device fixedly attached to a handle coupled to a proximal end of the flexible insertion tube, a tactile feedback in response to the selected measurement while deemphasizing a presentation of the selected measurement on the display.

There is additionally provided, in accordance with an embodiment of the present invention, a computer software product, the product including a non-transitory computer-readable medium, in which program instructions are stored, which instructions, when read by a computer, cause the computer to generate, during a medical procedure, first and second measurements corresponding to first and second signals received from first and second sensors mounted on a distal end of a flexible insertion tube configured for insertion into a body cavity, to present, on a display, the first and the second measurements, to accept an input selecting one of the presented measurements so as to generate a selected measurement, and to provide, by a haptic feedback device fixedly attached to a handle coupled to a proximal end of the flexible insertion tube, a tactile feedback in response to the selected measurement while deemphasizing a presentation of the selected measurement on the display.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

During a medical procedure where a catheter is placed within a patient's body, an operator manipulating the catheter typically pays attention to a large number of parameters (also referred to herein as measurements). The parameters may be tracked by different sensors (internal and external to the catheter), and values of the parameters are typically presented to the operator on one or more displays.

Examples of parameters which may be tracked include a location and an orientation of a distal tip of the catheter, temperatures and/or forces registered by the catheter, potentials measured by one or more electrodes on the distal tip, and power dissipated by the one or more electrodes. Depending on the number of parameters being tracked (e.g., the medical procedure may utilize multiple catheters), the parameters may be presented on one large screen or on multiple smaller screens, and tracking the parameters may become difficult as the number of parameters increase.

Embodiments of the present invention provide methods and system to present values of at least one of the parameters to the operator tactilely, thereby allowing the operator to track fewer parameters on the display. In some embodiments, a haptic feedback system is incorporated into a catheter handle which the operator uses to manipulate the catheter, and the system provides the operator with a tactile feedback that can vary according to a magnitude of one of the parameters being tracked. The operator may choose which parameter is to be used to provide the tactile feedback.

For example, a force parameter may be selected, the tactile feedback may be configured to provide a vibration having a frequency that changes as the force changes, and a force measurement presented on the display may then be de-emphasized or even removed from the display. Alternative parameters that may be tracked in a similar manner comprise a temperature of a feature selected by the operator, or a proximity to a feature selected by the operator.

In some embodiments, multiple haptic feedback systems may be incorporated into the handle, and a different parameter can be assigned to each of the haptic feedback systems. By increasing the number of parameters that are deemphasized on the display, embodiments of the present invention provide operator controlled mixed modality feedback that enables tracking of multiple parameters with greater ease, thereby enabling the operator to perform the medical procedure with greater accuracy and efficiency.

System Description

Figure 1:
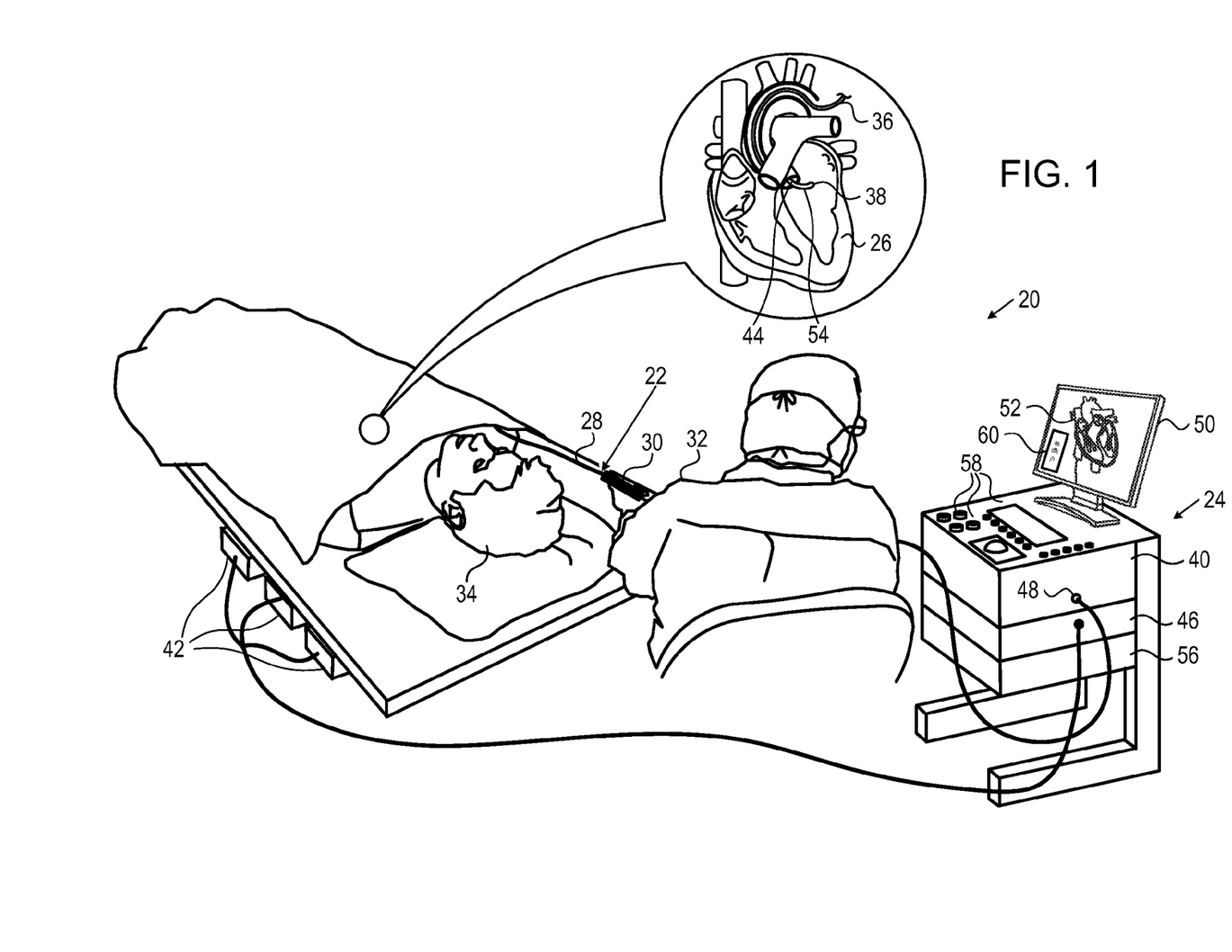
FIG. 1 is a schematic pictorial illustration of a medical system that implements operator controlled mixed modality feedback, in accordance with an embodiment of the present invention.

FIG. 1 is a schematic pictorial illustration of a medical system 20 that implements operator controlled mixed modality feedback, in accordance with an embodiment of the present invention. System 20 may be based, for example, on the CARTO™ system, produced by Biosense Webster Inc. (Diamond Bar, Calif.). System 20 comprises a probe 22, such as a catheter, and a control console 24. In the embodiment described hereinbelow, it is assumed that probe 22 is used for diagnostic or therapeutic treatment, such as for mapping electrical potentials in a heart 26 or performing ablation of heart tissue. Alternatively, probe 22 may be used, mutatis mutandis, for other therapeutic and/or diagnostic purposes in the heart or in other body organs.

Probe 22 comprises a flexible insertion tube 28, and a handle 30 coupled to a proximal end of the insertion tube. By manipulating handle 30, an operator 32 can insert probe 22 through the vascular system of a patient 34 so that a distal end of probe 22 enters a chamber of heart 26 and engages endocardial tissue at a desired location or locations. Probe 22 is typically connected by a suitable connector at its proximal end to console 24.

System 20 typically uses magnetic position sensing to determine position coordinates of distal end 36 inside heart 26. To determine the position coordinates, a driver circuit 40 in console 24 drives field generators 42 to generate magnetic fields within the body of patient 34. Typically, field generators 42 comprise coils, which are placed below the patient's torso at known positions external to patient 34. These coils generate magnetic fields in a predefined working volume that contains heart 26. A magnetic field sensor 44 (also referred to herein as a position sensor, and which is shown in more detail in FIG. 2) within distal end 36 of probe 22 generates electrical signals in response to these magnetic fields from the coils, thereby enabling console 24 to determine the position of distal end 36 within the chamber.

Although in the present example system 20 measures the position of distal end 36 using magnetic-based sensors, other position tracking techniques may be used (e.g., impedance-based sensors). Magnetic position tracking techniques are described, for example, in U.S. Pat. Nos. 5,391,199 and 6,690,963 referenced above, and in U.S. Pat. Nos. 5,443,489, 6,788,967, 5,558,091, 6,172,499 and 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

A signal processor 46 processes signals from sensor 44 in order to determine the position coordinates of distal end 36, which typically include both location and orientation coordinates. The method of position sensing described hereinabove is implemented in the above-mentioned CARTO™ system and is described in detail in the patents and patent applications cited above.

Signal processor 46 typically comprises a general-purpose computer, with suitable front end and interface circuits for receiving signals from probe 22 and controlling the other components of console 24. Processor 46 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 46 may be carried out by dedicated or programmable digital hardware components.

An input/output (I/O) interface 48 enables console 24 to interact with probe 22. Based on the signals received from probe 22 (via interface 48 and other components of system 20), processor 46 drives a display 50 to present operator 32 with an image 52 showing the position of distal end 36 in the patient's body, as well as status information and guidance regarding the procedure that is in progress.

In addition to presenting image 52, processor 46 may present, on the display, a list 60 of measurements that operator can monitor during the procedure. The measurements may be based on signals that probe 22 captures from heart 26, and conveys to console 24. Examples of measurements captured by probe 22 include, but are not limited to, electrical potential, force, temperature, distance from one or more pre-defined locations (e.g., a distance from a point on a map and/or a distance from an anatomical structure such as an esophagus), and a time at a location (typically when a distal tip 38 is relatively stationary).

Additionally or alternatively, the measurements may be based on signals that console 24 receives from a device external to probe 22. Examples of such external devices include, but are not limited to, blood pressure monitoring modules where the measurement indicates a blood pressure, irrigation modules where the measurement indicates an irrigation flow rate, an ablation module where the measurement indicates an ablation power and/or a time period wherein ablation is performed, electrocardiography (ECG) modules where the measurement indicates electrical activity of heart 26, and a timer module. Other types of modules will be apparent to those having ordinary skill in the art, and all such types are assumed to be included within the scope of the present invention.

In some embodiments, processor 46 monitors measurements received from position sensor 44 and a force sensor 54 within distal end 36 (force sensor 54 is shown in more detail in FIG. 2) during periods in which the catheter is believed to be pressing against endocardial tissue of heart 26. Processor 46 stores data representing image 52 in a memory 56. In some embodiments, using one or more input devices 58, operator 32 can manipulate image 52 and/or select a given measurement from list 60.

Alternatively or additionally, system 20 may comprise an automated mechanism (not shown) for maneuvering and operating probe 22 within the body of patient 34. Such mechanisms are typically capable of controlling both the longitudinal motion (advance/retract) of probe 22 and transverse motion (deflection/steering) of distal end 36 of the probe. In such embodiments, processor 46 generates a control input for controlling the motion of probe 22 based on the signals provided by the magnetic field sensor in the probe.

Although FIG. 1 shows a particular system configuration, other system configurations can also be employed to implement embodiments of the present invention, and are thus considered to be within the spirit and scope of this invention. For example, the methods described hereinbelow may be applied using position transducers of types other than the magnetic field sensor described above, such as impedance-based or ultrasonic position sensors. The term "position transducer" as used herein refers to an element mounted on probe 22 which causes console 24 to receive signals indicative of the coordinates of the element. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in therapeutic and diagnostic applications using not only catheters, but also probes of other types, both in the heart and in other body organs and regions.

Figure 2:
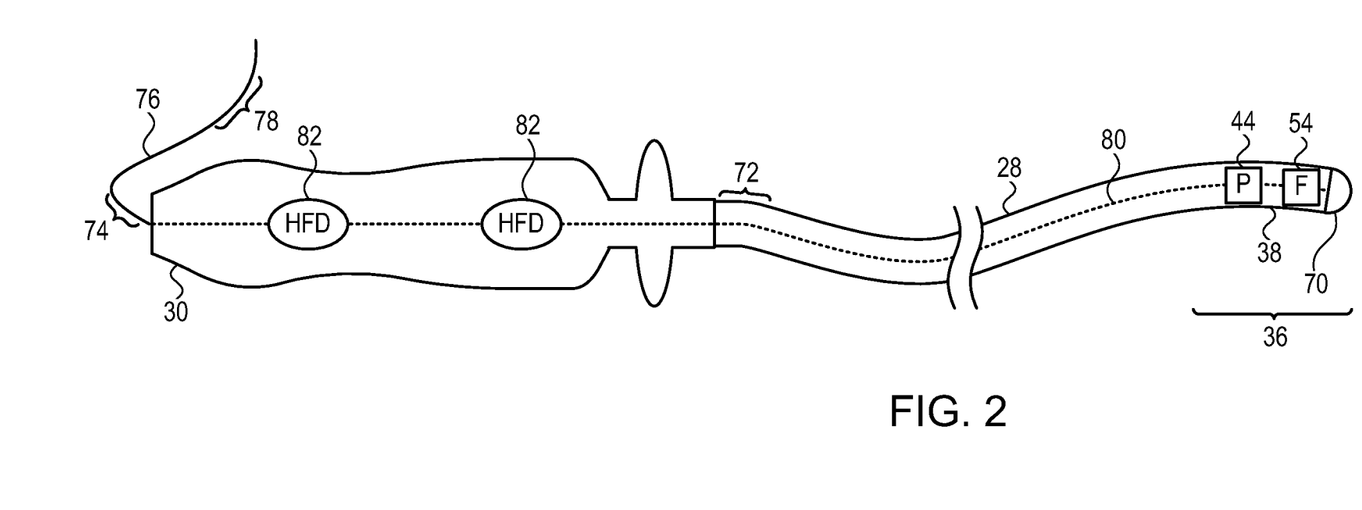
FIG. 2 is a schematic sectional view of a medical probe configured to generate tactile feedback, in accordance with an embodiment of the present invention.

FIG. 2 is a schematic sectional view of probe 22, in accordance with an embodiment of the present invention. Specifically, FIG. 2 shows functional elements of the probe. An ablation electrode 70 at distal tip 38 of the probe is typically made of a metallic material, such as a platinum/iridium alloy or another suitable material. Alternatively, multiple electrodes (not shown) may be positioned along the length of the probe.

Position sensor 44 transmits a signal to console 24 that is indicative of the position coordinates of distal end 36. Position sensor 44 may comprise one or more miniature coils, and typically comprises multiple coils oriented along different axes. Alternatively, position sensor 44 may comprise either another type of magnetic sensor, an electrode which serves as a position sensor, or position sensors of other types, such as impedance-based or ultrasonic position sensors.

In an alternative embodiment, the roles of position sensor 44 and magnetic field generators 42 may be reversed. In other words, driver circuit 40 may drive a magnetic field generator in distal end 36 to generate one or more magnetic fields. The coils in generators 42 may be configured to sense the fields and generate signals indicative of the amplitudes of the components of these magnetic fields. Processor 46 receives and processes these signals in order to determine the position coordinates of distal end 36 within heart 26.

Force sensor 54 measures a force applied by distal tip 38 to the endocardial tissue of heart 26 by conveying a signal to the console that is indicative of the force exerted by the distal tip on the intra-body tissue. In one embodiment, the force sensor may comprise a magnetic field transmitter and receiver connected by a spring in distal end 36, and may generate an indication of the force based on measuring the deflection of the spring. Further details of this sort of probe and force sensor are described in U.S. Patent Application Publications 2009/0093806 and 2009/0138007 referenced above. Alternatively, distal end 36 may comprise another type of force sensor.

Handle 30 is configured to be grasped by operator 32, and is coupled to a proximal end 72 of insertion tube 28 and a distal end 74 of a cable 76. A proximal end 78 of cable 76 is coupled to I/O interface 48. The distal end of cable 76 is coupled to position sensor 44, force sensor 54 and electrode 70 via a connecting cable 80 that is contained within insertion tube 28 and handle 30. While (for illustrative purposes) FIG. 2 shows a single connecting cable 80 coupling the electrode and the sensors to cable 76, there are typically multiple connecting cables contained within the insertion tube and the handle. Connecting cable 80 typically comprises a metallic conductor and/or an optical fiber.

In embodiments of the present invention one or more haptic feedback devices (HFDs) 82 are fixedly attached to handle 30 and are configured to provide operator 32 with tactile feedback during the procedure. The tactile feedback may comprise vibrations at different amplitudes (i.e., vibration intensity) and/or frequencies (i.e., vibrations/beats per minute). Haptic feedback devices 82 may be based on electroactive polymers (EAPs) such as those used in a ViviTouch™ system, produced by Artificial Muscle Inc. (Sunnyvale, Calif.).

Typically, the haptic feedback provided by a specific HFD is based on one of the measurements described above. For example, processor 46 may configure the specific HFD 82 to set an amplitude of a vibration based on a contact pressure between distal tip 38 and tissue in a body cavity (e.g., heart 26). Alternatively, processor 46 may configure the specific HFD to generate a frequency of the vibration based on the length of time the distal tip is applying the pressure.

In the example shown in FIG. 2, handle 30 comprises two haptic feedback devices 82. For example, a first haptic feedback device 82 may be positioned at a proximal end of the handle to convey tactile feedback to the operator's palm, and a second haptic feedback device 82, also referred to herein as an additional haptic feedback device 82, may be positioned at a distal end of the handle to convey tactile feedback to the operator's fingers.

In some embodiments, each of the two haptic feedback devices may be configured to convey tactile feedback based on first and second signals received from console 24. For example, processor 46 may select as a first measurement force, and as a second measurement ablation power. In this case, processor 46 can configure the first haptic feedback device 82 to convey tactile feedback based on first signals console 24 receives from force sensor 54 (corresponding to a first sensor), and the second haptic feedback device 82 to convey tactile feedback based on ablation power that console 24 delivers via electrode (corresponding to a second sensor).

Although FIG. 2 shows probe 22 with a single position sensor 44, embodiments of the present invention may utilize probes with more than one position sensor. Additionally or alternatively, probe 22 may comprise additional sensors such as a temperature sensor or devices such as an irrigation delivery system.

Operator Controlled Visual and Tactile Feedback

Figure 3:
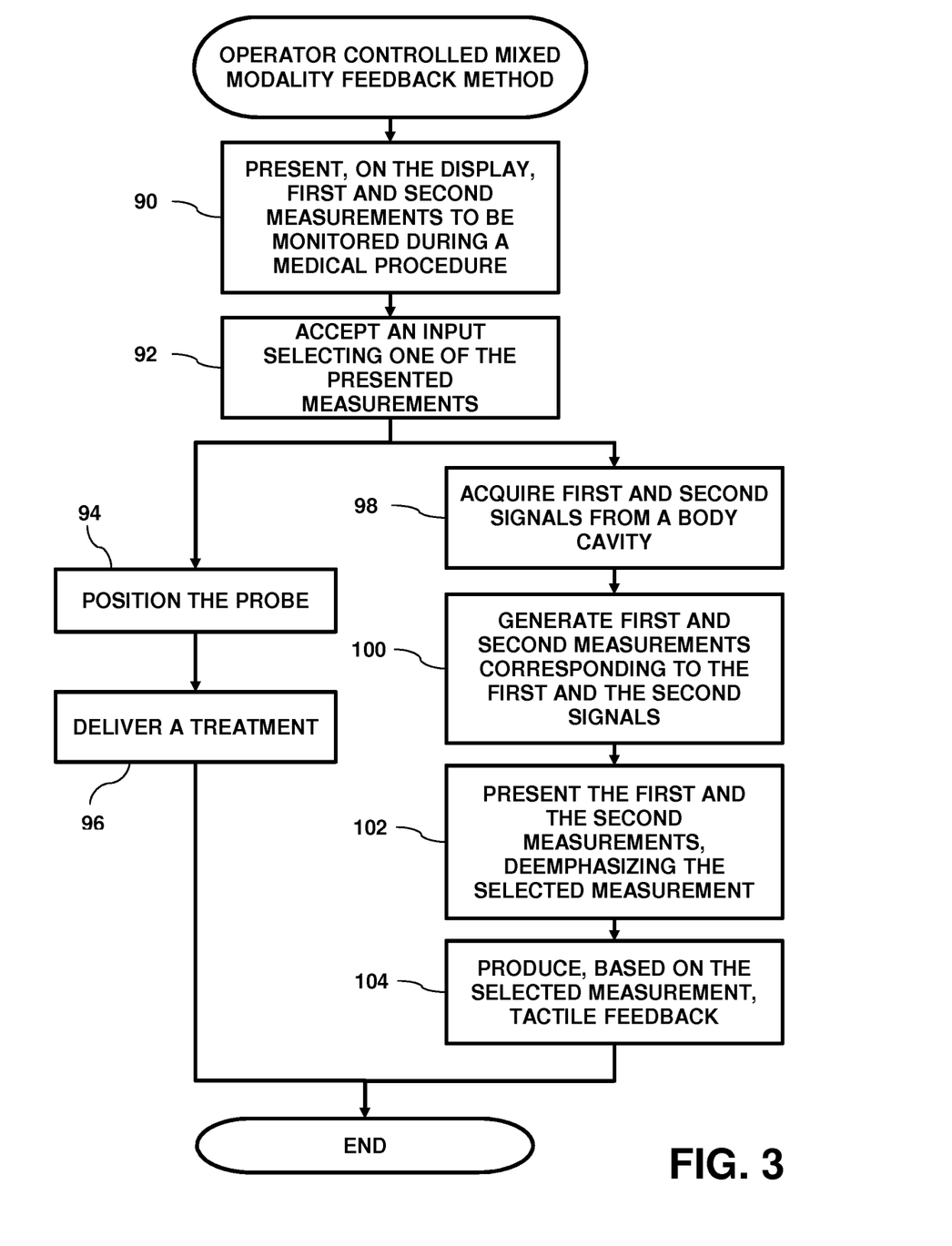
FIG. 3 is a flow diagram that schematically illustrates a method of operator controlled mixed modality feedback during a medical procedure, in accordance with an embodiment of the present invention.
Figure 4:
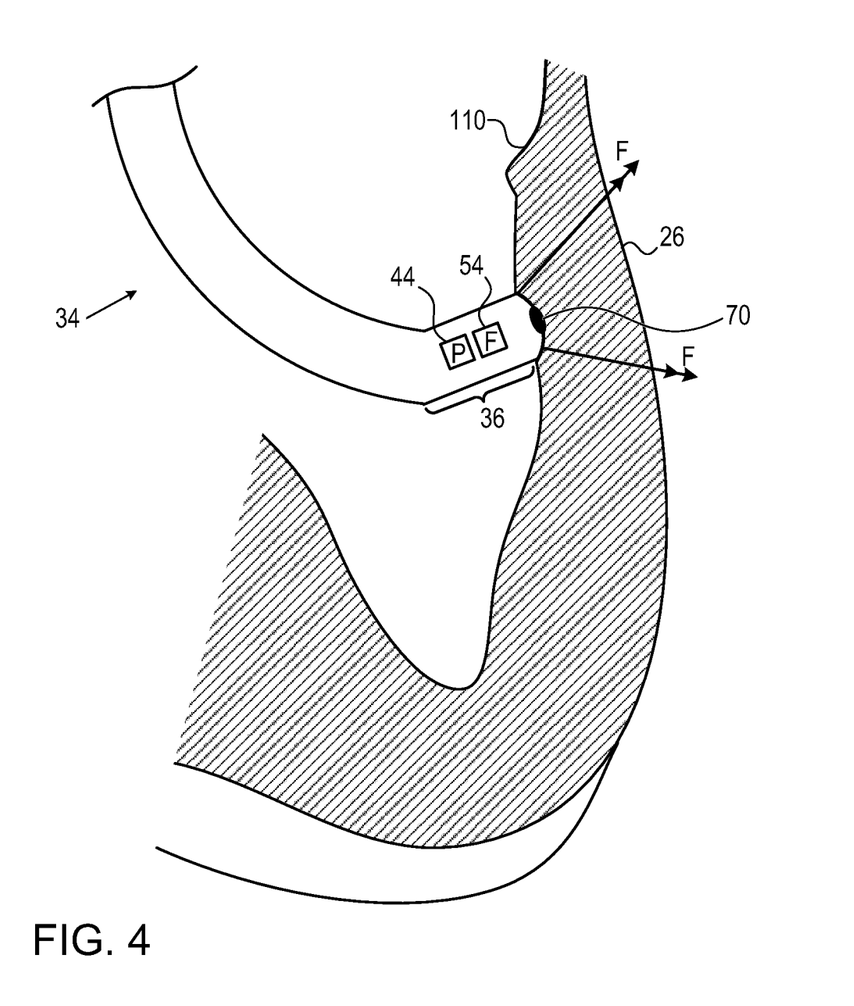
FIG. 4 is a schematic detail view showing a distal tip of the medical probe in contact with endocardial tissue, in accordance with an embodiment of the present invention.

FIG. 3 is a flow diagram that schematically illustrates a method of providing operator controlled mixed modality feedback during a medical procedure, and FIG. 4 is a schematic detail view showing distal tip 38 in contact with endocardial tissue 110 of heart 26, in accordance with an embodiment of the present invention. In the flow diagram described hereinbelow, steps 98-104 are performed simultaneously with steps 94-96.

In a presentation step 90, processor 46 presents list of measurements 60 on display 50. In the example described herein, list 60 comprises first and second measurements that correspond to first and second signals received from two different devices (e.g., position sensor 44 and force sensor 54). In an input step 92, operator 32 manipulates input devices 58 to select one of the presented measurements to be used for applying tactile feedback, and processor 46 accepts an input selecting the measurement. For example, operator 32 can select a force measurement for tactile feedback.

In a positioning step 94, operator 32 positions probe 22, and in a delivery step the probe delivers a treatment to heart 26. In the example shown in FIG. 4, operator 32 advances probe 22 so that distal tip 38 of the probe engages endocardial tissue 110, the distal tip exerts force F on the endocardial tissue. Upon engaging endocardial tissue 110, distal tip 38 can deliver a treatment (e.g., an ablation of the endocardial tissue).

As described supra, while operator positions the probe and delivers the treatment, the following steps 98-104 are performed simultaneously. In an acquire step 98, processor 46 acquires a first signal from position sensor 44 and a second signal, indicating a force F, from force sensor 54. In a generation step 100, the processor generates first and second measurements (i.e., position and force measurements) from the first and the second signals, and in a presentation step 102, processor 46 presents the first and the second measurements on display 50.

In embodiments of the present invention, processor 46 deemphasizes the measurement that is selected in step 92. For example, if the first and the second measurements comprise position and force measurements and operator 32 selects the force measurements in step 92, then processor 46 can deemphasize the force measurement on display 50 by applying any one or more of the following attributes:

Processor 46 can present the position measurement using a higher predetermined brightness than the brightness used to present the force measurement.

Processor 46 can decrease the brightness of the force measurement on the display by a predetermined amount, or remove the force measurement from the display.

Processor 46 can present the position measurement in a predetermined color such as yellow, and present the force measurement in a different predetermined color, such as green.

Processor 46 can present the force measurement using a smaller predetermined font size than a font size used to present the position measurement.

Other types of de-emphasis will be apparent to those having ordinary skill in the art, and all such types are assumed to be included within the scope of the present invention.

In a feedback step 104, while deemphasizing the force measurement on display 50, processor 46 conveys a feedback signal based on the force measurement (i.e., the selected measurement) to haptic feedback device 82, and the haptic feedback device produces tactile feedback based on the received signal. As described supra, the tactile feedback may comprise a vibration with varying amplitudes and/or frequencies.

In embodiments where handle 30 comprises an additional haptic feedback device 82, processor 46 may accept, in step 92, an additional input indicating an additional selected measurement. Upon receiving the additional input, processor 46 can deemphasize the additional selected measurement on the display, and direct the additional haptic feedback device to provide an additional tactile feedback in response to the additional selected measurement.

Additionally or alternatively, in embodiments where processor 46 receives signals from a device external to probe 22 (e.g., a blood pressure monitoring module), the processor may receive, a third signal from the device, and present, on the display, a third measurement corresponding to the third signal. In step 92, the received input may indicate the third measurement as the selected measurement.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
 a flexible insertion tube comprising a distal end for insertion into a body cavity;
 a first internal sensor mounted in the distal end and configured to acquire a first signal from the body cavity during a medical procedure;
 a second internal sensor mounted in the distal end and configured to acquire a second signal from the body cavity during the medical procedure;
 a control console having one or more input devices and a processor configured to present, on a display coupled to the control console, first and second measurements corresponding to the first and second signals, the processor further configured to receive an input from the one or more input devices selecting one of the first and second presented measurements so as to generate a selected measurement;

a handle coupled to a proximal end of the flexible insertion tube; and a haptic feedback device fixedly attached to the handle and configured to provide, a tactile feedback in response to the selected measurement while a presentation of the selected measurement is deemphasized on the display.

2. The apparatus according to claim 1, wherein the first and the second sensors are selected from a list comprising a position sensor, a force sensor, a temperature sensor and an electrode configured to measure electrical potential.

3. The apparatus according to claim 1, wherein the tactile feedback comprises a vibration, and wherein the haptic feedback device is configured to vary one of a frequency and an amplitude of the vibration.

4. The apparatus according to claim 1, wherein the processor is configured to receive an additional input selecting an additional one of the presented measurements so as to generate an additional selected measurement, and to deemphasize an additional presentation of the additional selected measurement on the display.

5. The apparatus according to claim 4, and comprising an additional haptic feedback device affixed to the handle and configured to provide, under direction from the processor, an additional tactile feedback in response to the additional selected measurement.

6. The apparatus according to claim 1, wherein the processor is configured to deemphasize the selected measurement by applying an attribute selected from a list comprising removing the selected measurement from the display, presenting the selected measurement using a predetermined font size, presenting the selected measurement using a predetermined color, and presenting the measurement using a predetermined brightness.

7. The apparatus according to claim 1, wherein the processor is configured to receive, from a device external to the flexible insertion tube, a third signal, and to present on the display a third measurement corresponding to the third signal, and wherein the input selects the third measurement.

8. The apparatus according to claim 7, wherein the device is selected from a list comprising a blood pressure module, an irrigation module, an ablation module, an electrocardiography module and a timer module.

9. A method, comprising:

generating, during a medical procedure, first and second measurements corresponding to first and second signals received from first and second sensors mounted on a distal end of a flexible insertion tube configured for insertion into a body cavity;

presenting, on a display coupled to a control console, the first and the second measurements;

receiving, by one or more input devices on the control console, an input selecting one of the presented measurements so as to generate a selected measurement; and providing, by a haptic feedback device fixedly attached to a handle coupled to a proximal end of the flexible insertion tube, a tactile feedback in response to the selected measurement while deemphasizing a presentation of the selected measurement on the display.

10. The method according to claim 9, wherein the first and the second sensors are selected from a list comprising a position sensor, a force sensor, a temperature sensor and an electrode configured to measure an electrical potential.

11. The method according to claim 9, wherein the tactile feedback comprises a vibration, and wherein the haptic feedback device is configured to vary one of a frequency and an amplitude of vibration.

12. The method according to claim 9, and comprising receiving an additional input selecting an additional one of the present measurements so as to generate an additional selected measurement, and deemphasizing an additional presentation of the additional selected measurement on the display.

13. The method according to claim 12, and comprising providing, by an additional haptic feedback device affixed to the handle, an additional tactile feedback in response to the additional selected measurement.

14. The method according to claim 9, wherein deemphasizing the selected measurement comprises applying an attribute selected from a list comprising removing the selected measurement from the display, presenting the selected measurement using a predetermined font size, presenting the selected measurement using a predetermined color and presenting the measurement using a predetermined brightness.

15. The method according to claim 9, and comprising receiving, from a device external to the flexible insertion tube, a third signal, and presenting on the display a third measurement corresponding to the third signal, and wherein the input selects the third measurement.

16. The method according to claim 15, wherein the device is selected from a list comprising a blood pressure module, an irrigation module, an ablation module, an electrocardiography module and a timer module.

17. A computer program product comprising computer-readable program code to be executed by one or more processors when retrieved from a non-transitory computer-readable medium, the program code including instructions to:

generate, during a medical procedure, first and second measurements corresponding to first and second signals received from first and second sensors mounted on a distal end of a flexible insertion tube configured for insertion into a body cavity;

present, on a display coupled to a control console, the first and the second measurements;

receive, by one or more input devices on the control console, an input selecting one of the presented measurements so as to generate a selected measurement; and provide, by a haptic feedback device fixedly attached to a handle coupled to a proximal end of the flexible insertion tube, a tactile feedback in response to the selected measurement while deemphasizing a presentation of the selected measurement on the display.

* * * * *